United States Patent [19]

Cahoy

[11] 3,974,223

[45] Aug. 10, 1976

[54] PROCESS FOR MANUFACTURE OF 3,5-DITERT.BUTYL-4-HYDROXYBENZALDEHYDE FROM 3,5-DITERT.BUTYL-4-HYDROXYBENZYL ALCOHOL

[75] Inventor: Roger P. Cahoy, Overland Park, Kans.

[73] Assignee: Gulf Oil Corporation, Pittsburgh, Pa.

[22] Filed: May 7, 1975

[21] Appl. No.: 575,554

[52] U.S. Cl. ............................................. 260/600 R
[51] Int. Cl.² .......................................... C07C 45/16

[58] Field of Search ................................... 260/600

[56] References Cited
UNITED STATES PATENTS

| | | | |
|---|---|---|---|
| 2,903,483 | 9/1959 | Berres | 260/600 |
| 3,833,660 | 9/1974 | Smith | 260/600 X |

*Primary Examiner*—Bernard Helfin
*Attorney, Agent, or Firm*—Carl A. Cline

[57] ABSTRACT

3,5-ditert.butyl-4-hydroxybenzyl alcohol is converted to the corresponding aldehydes by reaction with hexamethylenetetramine in aqueous acetic acid medium.

4 Claims, No Drawings

PROCESS FOR MANUFACTURE OF 3,5-DITERT.BUTYL-4-HYDROXYBENZALDEHYDE FROM 3,5-DITERT.BUTYL-4-HYDROXYBENZYL ALCOHOL

BACKGROUND OF THE INVENTION 3,5-ditert.butyl-4-hydroxybenzyl alcohol is an article of commerce, employed as an antioxidant of the hindered phenol type. The corresponding benzaldehyde is a desirable, reactive intermediate compound, used, for example, in the manufacture of pesticides of the benzylidenemalononitrile type.

Conversion of substituted benzyl alcohols to corresponding benzaldehydes by oxidation processes is known. (See for example, J. Org. Chem. v. 39, 3304 (1974) and J. Org. Chem. v. 26, 4814-16 (1961)). The oxidation of the alcohols involes problems with expensive reagents and disposal of inorganic waste products and yields, after purification, are not as good as desired. Oxidation of the corresponding benzyl chlorides is often considered to be a more economically attractive method of manufacturing the aldehydes. Another method of converting a limited class of benzyl halides of corresponding benzaldehydes is the Sommelet reaction in which the benzyl halide forms a quaternary salt by reaction with hexamethylenetetramine. The quaternary compound may then be hydrolyzed to yield the benzaldehyde and ammonia. The reaction is not a general one, sometimes failing for no apparent reason. (See "Survey of Organic Syntheses" by Calvin A. Buehler and Donald E. Pearson, pages 557-8, John Wiley & Sons, Inc. 1970) When this method is used to convert 3,5ditert.butyl-4-hydroxybenzyl chloride to the corresponding aldehyde, removal of colored, semisolid impurities from the product is time-consuming and inefficient.

SUMMARY OF THE INVENTION

I have discovered that 3,5-ditert.butyl-4-hydroxybenzyl alcohol reacts with hexamethylenetetramine in aqueous acetic acid medium to yield the corresponding benzaldehyde in high purity as a precipitated solid product. I have further discovered that reagents which are equivalent to a mixture of formaldehyde and ammonia, for example, formalin and ammonium acetate, may be substituted for the hexamethylenetetramine, so that the process may be operated with simple, inexpensive raw materials.

The absence of apparent side reactions and the ability to substitute formaldehyde and ammonia for the hexamethylenetetramine suggests that the conversion of the benzyl alcohol to the corresponding aldehyde occurs by a quite different mechanism from the conversion of the corresponding benzyl halide.

DESCRIPTION OF THE PREFERRED EMBODIMENTS

Briefly, the process of this invention comprises reacting 3,5-ditert.butyl-4-hydroxybenzyl alcohol with at least one molar equivalent of hexamethylenetetramine or reagents which are equivalent to a mixture of at least 6 moles of formaldehyde and at least 4 moles of ammonia in aqueous acetic acid reaction medium.

Preferably, at least one molar equivalent of hexamethylenetetramine or a mixture of formaldehyde and ammonium acetate equivalent thereto, is employed as a reagent, so as to avoid introduction of impurities into the product. Formaldehyde may be used in the form of commercial formalin solution or in pure form, or as a solid condensation product such as paraformaldehyde. Ammonia may be introduced directly into the acetic acid reaction medium, forming the acetate in situ. If this is not convenient, any of various readily available ammonium salts may be used.

The aqueous acetic acid reaction medium should contain at least 50 volume percent acetic acid in water (about 525 g. per liter). It is recommended practice to employ a reaction medium based on about 60 to about 85 volume percent aqueous acetic acid, preferably at least 65 volume percent, and containing an excess of hexamethylenetetramine of formaldehyde and ammonia and to re-use the liquid reaction medium one or more times after recovering the precipitated product. This procedure is more economical and minimizes waste disposal problems.

The reaction temperature should be high enough so that the reactants are in solution. Preferred reaction temperature is within the range of 65° to 115°C. Particularly preferred is reflux temperature at atmospheric pressure.

Examples which illustrate the best mode of operation of the invention are presented below.

EXAMPLE 1

A 12-liter reaction flask fitted with a mechanical stirrer, heating mantle, thermometer and water-cooled condenser with a gas exit line to a water bubble tube was charged with one liter of glacial acetic acid. With stirring, 280.4 g (2.0 moles) of hexamethylenetetramine was added. The temperature of the pot increased to 40°. To this stirred mixture was added a solution of 236.4 g (1.0 mole) of 3,5-ditert.butyl-4-hydroxybenzyl alcohol dissolved in 1 liter of acetic acid. After this addition, the pot temperature dropped to 30° and a clear solution was observed. The addition of one liter of water to the stirred solution produced a heavy orange precipitate along with a small increase in the pot temperature. With good agitation, slow external heating was initiated. All solid material was dissolved when the temperature reached 65°-70°. At a pot temperature of 100°-102° small yellow crystals were noted on the sides of the reaction flask. Heating was continued to the reflux temperature (107°). A total of 1.25 hours was recorded to reach the reflux temperature. The quantity of precipitated crystalline solids slowly increased and slow gas evolution was noted. When the gas stream was conducted through a saturated aqueous solution of calcium oxide, a white precipitate formed. No reaction occurred when a 2,4-dinitrophenylhydrazine solution was contacted with the exit gas. After two hours of reflux, the heating mantle was removed. An ice bath was employed to cool the stirred reaction mixture to 25°. The stirrer was stopped and a "fritted-glass" cylindrical filter stick was placed in the reaction flask. The filtrate was conducted by an attached tube to another vessel under reduced pressure from a vacuum source. This filtrate (2280 ml; 2477 g) was retained for use as the recycled solvent for the next example described below. The reaction flask was charged with 2500 ml of water and stirred for five minutes. The wash water was withdrawn by means of the cylindrical filter stick and the filtrate was discarded. An additional 2500 ml of water was added. After stirring, the reaction slurry was poured on a vacuum filter. The filtration rate was rapid.

A 500 ml charge of water was used to rinse the reaction flask and was then transferred to the filter. After most of the liquid had been removed from the filter cake, the filtrate was discarded and the product was transferred to a glass tray. After air drying overnight, the material was placed in a vacuum oven at 60°–65° for three hours. There was obtained 205 g of light yellow crystalline material, m.p. 189°–191°. By GLC analysis, the product was judged to be 96.8% 3,5-ditert.butyl-4-hydroxybenzaldehyde. The infrared and nuclear magnetic resonance spectra are identical when compared to those of authentic material. The yield was 84.7%.

EXAMPLE 2

The Preparation of 3,5-ditert.butyl-4-hydroxybenzaldehyde Employing Recycled Reaction Filtrate A 12-liter reaction flask fitted as previously described was charged with 2280 ml (2477 g) of the initial filtrate from the above described reaction. With stirring, the reaction flask was charged with 106.5 g (0.76 mole) of hexamethylenetetramine. As the amine dissolved, there was a small exothermic response. To this solution was added 179.6 g (0.76 mole) of 3,5-ditert.butyl-4-hydroxybenzyl alcohol. There was no apparent reaction and when external heating had increased the pot temperature to 65°–70°, the slurry formed a clear solution. With controlled heating, reflux (108°) was attained after 1.25 hours with product precipitation and gas evolution recorded beginning at 104°. After two hours at reflux, the reaction mixture was cooled to 25°. The product was separated from the mother liquor and washed as described above. After drying in the vacuum oven, there was obtained 164 g of light yellow crystalline 3,5-ditert.butyl-4-hydroxybenzaldehyde, m.p. 191°–93°. The product was submitted for GLC analysis and found to be equivalent to the analytical standard (100%). The yield was 92.1%.

EXAMPLE 3

The Preparation of 3,5-ditert.butyl-4-hydroxybenzaldehyde Employing Formalin and Ammonium Acetate This example illustrates the substitution of an equivalent mixture of reagents for hexamethylenetetramine in the reaction with 3,5-ditert.butyl-4-hydroxybenzyl alcohol.

A 500 ml reaction flask fitted with a mechanical stirrer, heating mantle, thermometer and water-cooled condenser was charged with 100 ml of glacial acetic acid and 17 ml of water. To the stirred solution there were added 30.8 g (0.4 mole) of ammonium acetate, 48.7 g of 37% formalin (0.60 mole formaldehyde) and 11.8 g (0.05 mole) of 3,5-ditert.butyl-4-hydroxybenzyl alcohol. The reaction flask was equipped with a take-off head to remove the methanol which is present in commercially available formalin. The mixture was refluxed (100°–2°) for 2 hours. The cooled mixture was poured on a vacuum filter and the product cake was washed with water. After drying, there was obtained 8.0 g of crystalline 3,5-ditert.butyl-4-hydroxybenzaldehyde, m.p. 191°–93° (68.4%).

In further examples mole ratios of reactants and concentration of acetic acid were varied to illustrate the general effect of these variables on the result. The same general procedure was employed as in Example 1. These examples are summarized in the following table:

| Example No. | Mole Alcohol[1] | Mole HMT[2] | ml HOAC | ml Water | % yield of Product[3] | Remarks |
|---|---|---|---|---|---|---|
| 4 | 0.10 | 0.10 | 200 | 100 | 76 | refluxed two hours |
| 5 | 0.10 | 0.30 | 200 | 100 | 87 | refluxed two hours |
| 6 | 0.20 | 0.40 | 300 | 300 | 76 | impure product |

[1]3,5-di-*tert*.butyl-4-hydroxybenzyl alcohol
[2]hexamethylenetetramine
[3]3,5-di-*tert*,butyl-4-hydroxybenzaldehyde The method of this invention gives extraordinarily good results in the manufacture of the specified product but should not be construed as applicable to conversion of all substituted benzyl alcohols. By way of example, the process has been shown to fail to give useful results with 4-chlorobenzyl alcohol, 4-methoxybenzyl alcohol or 4-nitrobenzyl alcohol.

I claim:

1. The method of manufacturing 3,5-ditert.butyl-4-hydroxybenzaldehyde comprising reacting 3,5-ditert.butyl-4-hydroxybenzyl alcohol with at least one molar equivalent of hexamethylenetetramine or a mixture of at least 6 moles of formaldehyde and at least 4 moles of ammonia in aqueous acetic acid reaction medium of at least 50 volume percent concentration at a temperature within the range of 65° to 115°C sufficient to assure solution of the reactants and recovering said 3,5-ditert.butyl-4-hydroxybenzaldehyde from the resulting reaction mixture.

2. The method of manufacturing 3,5-ditert.butyl-4-hydroxybenzaldehyde comprising reacting 3,5-ditert.butyl-4-hydroxybenzyl alcohol with at least 1 molar equivalent of hexamethylenetetramine or a mixture of at least 6 moles of formaldehyde and four moles of ammonia in aqueous acetic acid reaction medium of about 60 to 85 volume percent concentration at reflux temperature and recovering said 3,5-ditert.butyl-4-hydroxybenzaldehyde from the resulting reaction mixture.

3. The method of manufacturing 3,5-ditert.butyl-4-hydroxybenzaldehyde comprising reacting 3,5-ditert.butyl-4-hydroxybenzyl alcohol with at least 1 molar equivalent of hexamethylenetetramine in aqueous acetic acid reaction medium of about 60 to 85 volume percent concentration at reflux temperature at atmospheric pressure and recovering said 3,5-ditert.butyl-4-hydroxybenzaldehyde from the resulting reaction mixture.

4. The method of manufacturing 3,5-ditert.butyl-4-hydroxybenzaldehyde comprising the steps, a. reacting 3,5-ditert.butyl-4-hydroxybenzyl alcohol with at least one molar equivalent of hexamethylenetetramine or a mixture of at least 6 moles of formaldehyde and at least 4 moles of ammonium acetate in aqueous acetic acid reaction medium of at least 65 volume percent concentration at reflux temperature at atmospheric pressure, b. recovering said 3,5-ditert.butyl-4-hydroxybenzaldehyde from the resulting reaction mixture by filtation, and c. recycling filtrate from step (b) to be used as at least a portion of the reaction medium in step (a).

* * * * *